(12) United States Patent
Shen et al.

(10) Patent No.: US 7,286,639 B2
(45) Date of Patent: Oct. 23, 2007

(54) FOCAL SPOT SENSING DEVICE AND METHOD IN AN IMAGING SYSTEM

(75) Inventors: Bing Shen, Cary, NC (US); David Michael Hoffman, New Berlin, WI (US); Thomas Louis Toth, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 18 days.

(21) Appl. No.: 10/707,422

(22) Filed: Dec. 12, 2003

(65) Prior Publication Data

US 2005/0129175 A1    Jun. 16, 2005

(51) Int. Cl.
     *H05G 1/64*      (2006.01)
     *G01T 1/24*      (2006.01)
     *G01T 1/29*      (2006.01)

(52) U.S. Cl. .................. 378/98.8; 378/19; 250/370.09; 250/370.1

(58) Field of Classification Search .................. 378/16, 378/19, 98.8, 137, 138; 250/370.09, 370.1
See application file for complete search history.

(56) References Cited

U.S. PATENT DOCUMENTS

| 3,107,276 | A | * | 10/1963 | Cohen | 348/162 |
| 4,559,639 | A | * | 12/1985 | Glover et al. | 378/19 |
| 4,827,494 | A | * | 5/1989 | Koenigsberg | 378/138 |
| 4,991,189 | A | * | 2/1991 | Boomgaarden et al. | 378/4 |
| 5,065,420 | A | * | 11/1991 | Levene | 378/137 |
| 5,131,021 | A | | 7/1992 | Gard et al. | 378/19 |
| 5,204,533 | A | * | 4/1993 | Simonet | 250/361 R |
| 5,469,429 | A | * | 11/1995 | Yamazaki et al. | 378/19 |
| 5,550,378 | A | * | 8/1996 | Skillicorn et al. | 250/367 |
| 5,550,886 | A | * | 8/1996 | Dobbs et al. | 378/19 |
| 5,550,889 | A | | 8/1996 | Gard et al. | 378/113 |
| 5,566,220 | A | * | 10/1996 | Saito et al. | 378/138 |
| 5,608,776 | A | * | 3/1997 | Hsieh | 378/145 |
| 5,657,364 | A | * | 8/1997 | Pfoh | 378/137 |
| 5,680,427 | A | * | 10/1997 | Dobbs et al. | 378/19 |
| 5,684,855 | A | * | 11/1997 | Aradate et al. | 378/4 |
| 5,706,326 | A | | 1/1998 | Gard | 378/19 |
| 5,949,843 | A | * | 9/1999 | Tamaki et al. | 378/17 |
| 6,014,420 | A | * | 1/2000 | Ooi | 378/19 |

(Continued)

*Primary Examiner*—Allen C. Ho
(74) *Attorney, Agent, or Firm*—Cantor Colburn LLP

(57) ABSTRACT

A focal spot sensing device includes: a housing that resists x-ray beams; an opening disposed in a wall of the housing that allows an x-ray beam to enter the housing; and a sensor device disposed in the housing that interprets a position of the x-ray beam for calculating a position of a focal spot. An imaging system includes: an x-ray source that produces an x-ray beam and has a focal spot; a detector array that receives the x-ray beam and includes a focal spot sensing device, the focal spot sensing device includes: a housing that resists x-ray beams; an opening disposed in a wall of the housing that allows the x-ray beam to enter the housing; and a sensor device disposed in the housing that interprets a position of the x-ray beam for calculating a position of the focal spot. A method for sensing a focal spot, the method includes: receiving an x-ray beam into an opening of a focal spot sensing device; interpreting a position of the x-ray beam; and calculating or measuring a position of a focal spot.

18 Claims, 2 Drawing Sheets

U.S. PATENT DOCUMENTS

| | | | |
|---|---|---|---|
| 6,056,437 A * | 5/2000 | Toth | 378/205 |
| 6,094,469 A * | 7/2000 | Dobbs et al. | 378/19 |
| 6,114,703 A * | 9/2000 | Levin et al. | 250/367 |
| 6,118,840 A | 9/2000 | Toth et al. | 378/19 |
| 6,215,844 B1 * | 4/2001 | Adachi et al. | 378/19 |
| 6,256,364 B1 * | 7/2001 | Toth et al. | 378/4 |
| 6,362,481 B1 * | 3/2002 | Warren | 250/368 |
| 6,370,218 B1 | 4/2002 | Toth et al. | 378/19 |
| 6,380,541 B1 * | 4/2002 | Laine et al. | 250/368 |
| 6,411,672 B1 * | 6/2002 | Sasaki et al. | 378/19 |
| 6,628,984 B2 * | 9/2003 | Weinberg | 600/436 |
| 6,652,143 B2 * | 11/2003 | Popescu | 378/207 |
| 2004/0104349 A1 * | 6/2004 | Chugg | 250/370.01 |
| 2005/0265521 A1 * | 12/2005 | Deuringer et al. | 378/138 |

\* cited by examiner

FOCAL SPOT SENSING DEVICE AND METHOD IN AN IMAGING SYSTEM

BACKGROUND OF THE INVENTION

This invention relates generally to a method and apparatus for CT imaging and other radiation imaging systems and, more particularly, to determining the focal spot position of an imaging system, providing a real-time feedback input to system for correction or calibration of focal spot induced errors.

In at least some "computed tomography" (CT) imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated beam radiation received at a detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In third generation CT systems, the x-ray source and the detector array are rotated with a gantry within the imaging plane and around the object to be imaged, so the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent to the scintillator. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In the third generation CT scanners, tube focal spot has been regarded as a stationary x-ray source with respect to x-ray detector. However, tube focal spot motion relative to detector is unavoidable due to x-ray generation mechanism and tremendous stress induced by extreme thermal and gravitational load operating conditions.

It is desirable to have a stationary tube focal spot. Otherwise, detector collimator plate aiming accuracy has to be maintained so that detector would have a linear response with respect to any focal spot motion in directions, which are perpendicular to collimator plate. In some circumstances, the required tolerance on deviation from design nominal is less than 1 micron, well beyond capabilities of existing manufacturing technologies.

To mitigate difficulty of maintaining collimator plate aiming accuracy, many manufacturers adopted a method of purposely misaligning (skewing) plates to focal spot. However, this would have other adverse affects. Even with 'misaligning' design, plate-aiming accuracy still remains at the limit of current manufacturing technology. Significant yield loss occurs just for collimator plate flatness (plate bow) requirement. For 40 mm Z-coverage detector collimator, plate yield due to plate flatness specification may be less than 50%.

To maintain image quality on low contrast detectability, CT number accuracy and artifact minimization, CT detector collimator scatter rejecting capability requirement increases with increasing scan coverage in the Z-axis. One option is to increase collimator aspect ratio by increasing plate height in the direction of x-ray projection. Plate height increase, however, presents a major challenge for detector design and manufacturing, since detector sensitivities to focal spot motion increases at same rate.

Tube focal spot motion induces not only beam position change at the detector, but also the X-ray incident angle change. Although beam position sensing and tracking provide adequate performance regarding dose saving and detector Z-axis non-uniform correction, it would be desirable to be able to measure focal spot position directly so that both beam position and incident angle can be captured. It has been discovered that x-ray beam incident angle, in addition to beam position, at the detector has significant impact on its performance. It is therefore seen to be desirable to measure the tube focal spot position with respect to detector.

If the position of the focal spot can be accurately measured in real time, control methods are known in the art to reposition the focal spot within the tube using magnetic or electrical fields, for example U.S. Pat. No. 5,550,889 or software correction algorithms can be employed during reconstruction to compensate for the undesired effects.

BRIEF DESCRIPTION OF THE INVENTION

The above-described drawbacks and deficiencies are overcome or alleviated by a focal spot sensing device. In an exemplary embodiment, a focal spot sensing device includes: a housing that resists x-ray beams; an opening disposed in a wall of the housing that allows an x-ray beam to enter the housing; and a sensor device disposed in the housing that interprets a position of the x-ray beam for calculating a position of a focal spot. In another exemplary embodiment, a focal spot sensing device includes: a housing that resists x-ray beams; an opening disposed in the housing that allows an x-ray beam to enter the housing; and means for calculating a position of a focal spot.

In another exemplary embodiment, an imaging system includes: an x-ray source that produces an x-ray beam and has a focal spot; a detector array that receives the x-ray beam and includes a focal spot sensing device, the focal spot sensing device includes: a housing that resists x-ray beams; an opening disposed in a wall of the housing that allows the x-ray beam to enter the housing; and a sensor device disposed in the housing that interprets a position of the x-ray beam for calculating a position of the focal spot.

In another exemplary embodiment, a method for sensing a focal spot, the method includes: receiving an x-ray beam into an opening of a focal spot sensing device; interpreting a position of the x-ray beam; and calculating a position of a focal spot.

The above discussed and other features and advantages of the present invention will be appreciated and understood by those skilled in the art from the following detailed description and drawings.

BRIEF DESCRIPTION OF THE DRAWINGS

Referring to the exemplary drawings wherein like elements are numbered alike in the several Figures.

DETAILED DESCRIPTION OF THE INVENTION

Figure 1:
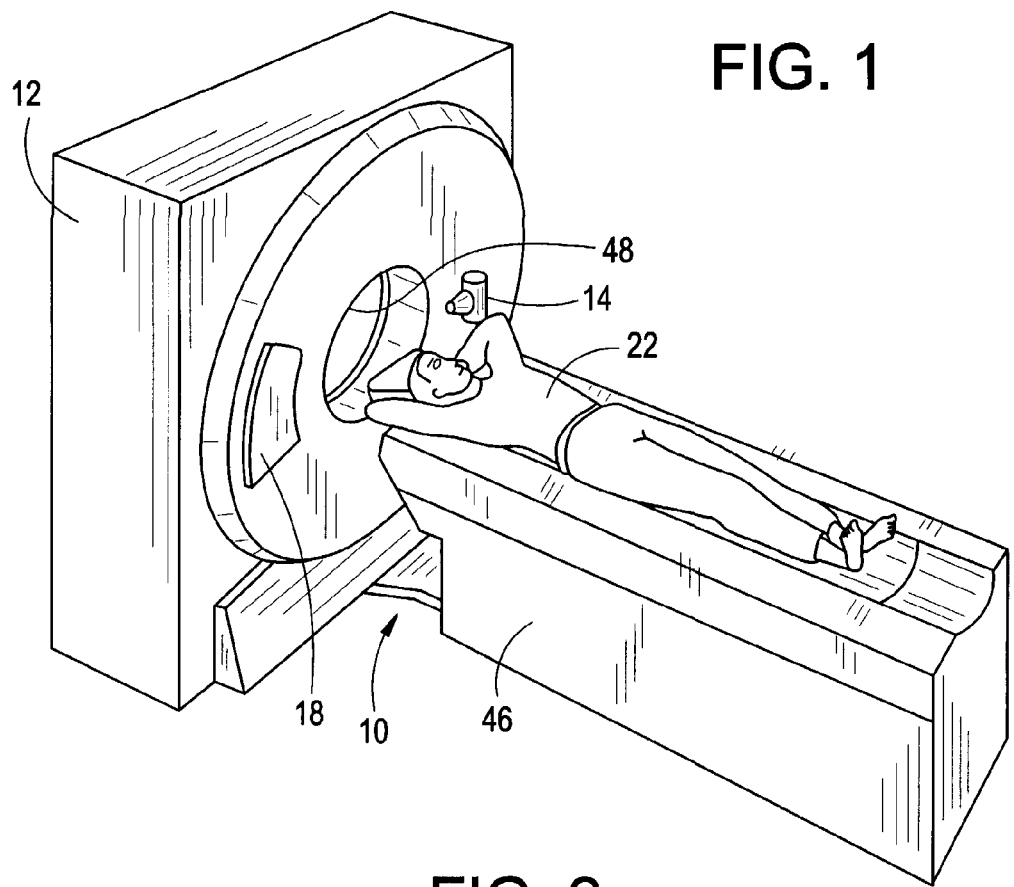
FIG. 1 is a pictorial view of a CT imaging system.
Figure 2:
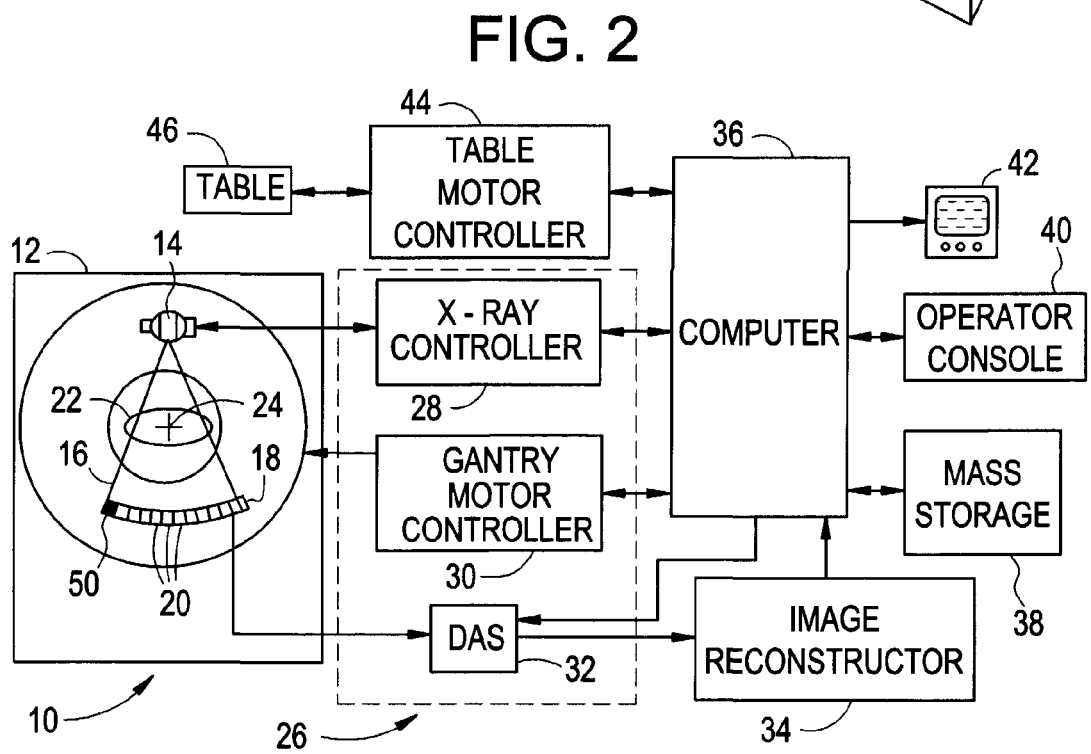
FIG. 2 is a block schematic diagram of the system illustrated in FIG. 1.

Referring to FIGS. 1 and 2, a computed tomography (CT) imaging system 10 is shown as including a gantry 12 representative of a CT scanner, such as a "third generation" CT scanner for example. Gantry 12 has an x-ray source 14 that projects a beam of x-rays 16 toward a detector array 18 on the opposite side of gantry 12. Detector array 18 is formed by detector elements 20, which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. In an embodiment, control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36, which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
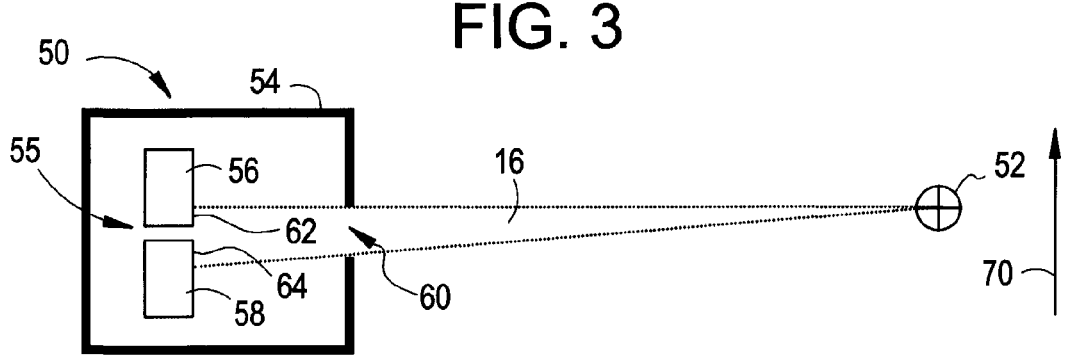
FIG. 3 is a side view of an embodiment for sensing a position of a focal spot.

FIG. 3 is an embodiment for a focal spot sensing device 50. In this embodiment, the device 50 senses the position of a focal spot 52 only in one dimension, such as the z-axis. Referring to FIGS. 1-3, the device 50 is located on the detector array 18 within the beam of x-rays 16 and will preferably be located along an edge of the detector array 18. In one embodiment, the device 50 will replace one of the detector elements 20. The focal spot 52 is located behind the x-ray source 14, or in a direction opposite from the beam of x-rays 16.

Referring again to FIG. 3, the device 50 includes an x-ray shielding housing 54, which is made of material that resists x-ray beams, such as tungsten or lead. In an exemplary embodiment, the housing 54 is a size that can be incorporated at an edge of the detector array, for instance, approximately 1 inch by 1 inch by 1 inch. A sensor device 55, which includes two x-ray detector elements 56 and 58, reside inside the housing 54. The detector elements 56 and 58 create electrical current outputs, which are proportional to the input x-ray they received. The detector elements 56 and 58 can be any type of detector elements that can detect an x-ray beam, such as a scintillator combined with a photodiode.

The device 50 includes an opening 60 that allows the x-ray beams 16 to enter the housing 54 and strike the detector elements 56 and 58. Opening 60 is positioned so as to face the focal spot 52. In addition, opening 60 is sized large enough so that the x-ray beams strike both detector elements 56 and 58. Meanwhile, opening 60 should keep small enough so that the x-ray beam is less than the total sensitive area of elements 56 and 58.

The detector elements 56 and 58 monitor the position of the x-ray focal spot 52 by measuring the position of x-ray beam falling on them. The detector elements 56 and 58 sense and measure the amount of x-ray that strikes them. As focal spot 52 moves along the z-axis 70, areas 62 and 64, which are the areas of x-ray falling on detector elements 56 and 58 respectively, would change. As a result, the comparison of output changes between detector elements 56 and 58 can be used as a position indicator for focal spot 52 along the z-axis 70.

Figure 4:
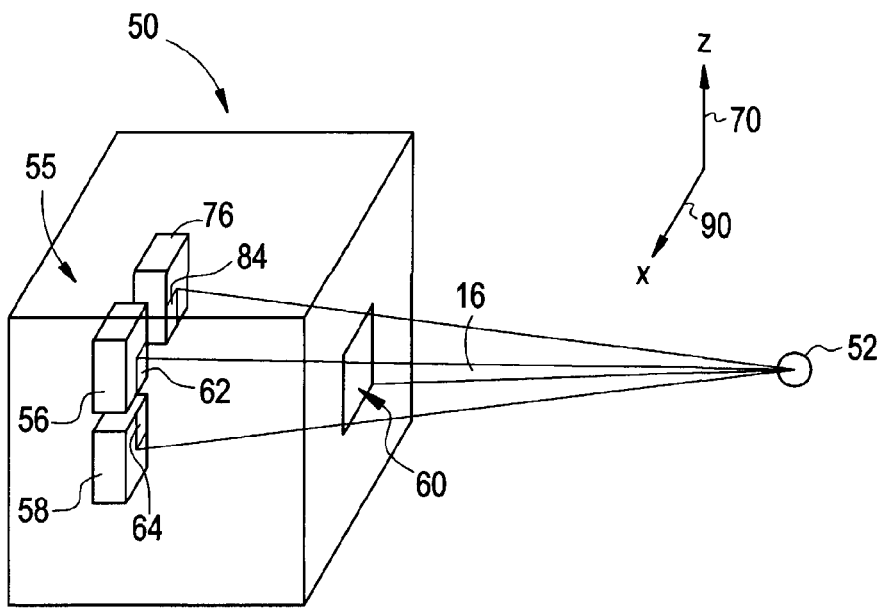
FIG. 4 is a side perspective view of another embodiment for sensing a position of a focal spot.

FIG. 4 illustrates an extended embodiment of the device 50, enabling focal spot position measurement in two dimensions. In this embodiment, the device 50 includes detector elements 56, 58, and 76. Opening 60 is sized so as to allow the x-ray beam to strike all three detector elements 56, 58, and 76 simultaneously while keeping the overall beam size through opening 60 less than the total sensitive areas of three detector elements. The detector elements 56, 58, and 76 sense the amount of x-ray that strikes the elements 56, 58, and 76 by measuring areas 62, 64, and 84 of x-ray along the front of the elements 56, 58, and 76. Thus, by adding detector element 76, the movement of the focal spot 52 in the x-axis 90 is also measured.

Figure 5:
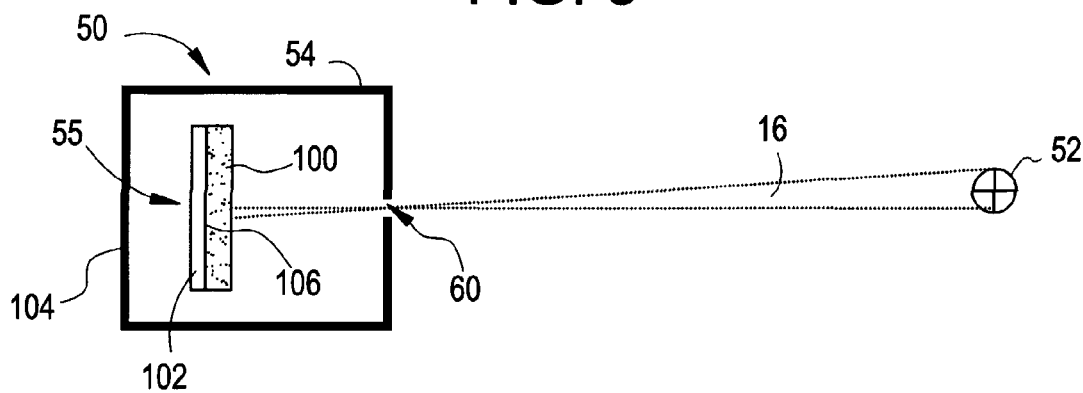
FIG. 5 is a side view of another embodiment for sensing a position of a focal spot.

FIG. 5 illustrates an alternative embodiment of the device 50. In this embodiment, device 50 includes the housing 54 and the opening 60, which is approximately the size of a pinhole such that the x-ray beam at the surface of photodiode 102 is less than the total sensitive area of photodiode 102. In an exemplary embodiment, the pinhole is approximately 0.5 mm in diameter. A fluorescent screen 100 faces the opening 60 and a photodiode 102 is located between a back wall 104 of the housing 54 and the fluorescent screen 100. In an exemplary embodiment, there is no space and/or air gaps between the fluorescent screen 100 and the photodiode 102. It is noted that the fluorescent screen 100 and the photodiode 102 will operate if there is a space and/or air gaps between the fluorescent screen 100 and the photodiode 102; however, in an embodiment the efficiency of the fluorescent screen 100 and the photodiode 102 increase when the space is eliminated and the air gaps are reduced and/or eliminated.

The fluorescent screen 100 is positioned to receive x-ray passing through the pin hole and a position sensitive photodiode 102 optically attached the screen 100 reside inside the housing 54. Optical attachment between screen 100 and photodiode 102 can be accomplished using a transparent epoxy layer 106 so that most visible light emission created by x-ray striking screen 100 would be coupled to photodiode 102. The transparent epoxy layer also allows the fluorescent screen 100 and the photodiode 102 to be held together.

The x-ray beam 16 travels through the opening 60 and strikes the fluorescent screen 100. The location of the x-ray beam 16 striking the fluorescent screen 100 glows with a light. The light is coupled to position sensitive photodiode 102 and its position is read out. As such, as the focal spot 52 moves, the light on the fluorescent screen 100 moves, which then the position sensitive photodiode 102 reads. The focal spot 52 movement can be determined, because as the focal spot 52 moves, the position of the x-ray beam 16, and light emission, created by x-ray beam 16 striking the fluorescent screen 100 moves, which is then read by the position sensitive photodiode 102.

In any of the embodiments described above, the focal spot movement is measured and known. Thus, the measurement can be used as a feedback for hardware to maintain stationary relationship between the focal spot and the detector array. In addition, the measurement can be provided to the computer 36 (see FIGS. 1 and 2) and used to compensate for focal spot motion induced error in the response of the detector 20. The relationship is determined by mechanical geometries of components of detector 20 and thus will not change during the operation life of detector 20. As the CT medical scans are performed on a patient, the position of focal spot 52 is measured for every view of the data acquisition. Using the relationship between detector response and focal spot position measured as detector is integrated, it becomes possible for computer 36 to separate and to eliminate detector response change due to focal spot motion from detector response change due to scanned patient.

The advantages of the device 50 are that there is a reduced cost for manufacturing the CT scanner because there is a less stringent requirement for collimator plate aiming accuracy and plate flatness. There is also improved dose efficiency because detector skew is unnecessary. There is also an enhanced image quality since device 50 enables higher aspect ratio of collimator geometry, which translates to stronger scatter rejection capabilities. This is also important for future CT development aiming at wider scan coverage. In addition, when hardware maintains a stationary relationship between the detector array and the focal spot, the need for beam tracking is eliminated. X-ray beam dimension can be better matched with detector geometry so that dose efficiency can be further improved.

Moreover, the preceding description describes the various embodiments of the present invention. Although the invention has been described and illustrated in detail, it is to be clearly understood that the same is intended by way of illustration and example only and is not to be taken by way of limitation. In addition, while the system has been described with reference to a CT scanner, the focal spot sensing device would be applicable to any system of which the focal spot motion induces errors.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims

The invention claimed is:

1. A focal spot sensing device comprising:
a housing that resists x-ray beams;
an opening disposed in a wall of the housing that allows an x-ray beam to enter the housing; and
a sensor device disposed in the housing for interpreting a position of the x-ray beam for calculating a position of a focal spot, the sensor device being disposed in the housing such that an area of the x-ray allowed to fall on the sensor device changes in both position and size at the sensor device in response to movement of the focal spot in a plane parallel to the plane of the sensor device;
wherein the opening is sized such that the x-ray beam at a surface of the sensor device is less than a total sensitive area of the sensor device;
wherein the sensor device includes at least three detector elements;
wherein a first and a second of the at least three detector elements are arranged next to each other and are aligned with a first axis parallel to the plane of the sensor device, and the first and a third of the at least three detector elements are arranged next to each other and are aligned with a second axis parallel to the plane of the sensor device, the second axis being perpendicular to the first axis;
wherein the opening and the at least three detector elements are disposed such that the x-ray beam passing through the opening is allowed to strike more than two of the at least three detector elements, but only on just a portion of each of the at least three detector elements capable of receiving the x-ray beam, the portion being less than 100% of a sensitive area of an associated detector element;
wherein a change in output signal of each detector element of the sensor device is responsive to a change in position and size of the area of x-ray allowed to fall on each detector element of the sensor device in response to the movement of the focal spot; and
wherein the change in output signal is a position indicator for the focal spot in two dimensions.

2. The device of claim 1, wherein the at least two detector elements include a scintillator and a photodiode.

3. A focal spot sensing device comprising:
a housing that resists x-ray beams;
an opening disposed in a wall of the housing that allows an x-ray beam to enter the housing; and
a sensor device disposed in the housing for interpreting a position of the x-ray beam for calculating a position of a focal spot, the sensor device being disposed in the housing such that an area of the x-ray allowed to fall on the sensor device changes in both position and size at the sensor device in response to movement of the focal spot in a plane parallel to the plane of the sensor device;
wherein the opening is sized such that the x-ray beam at a surface of the sensor device is less than a total sensitive area of the sensor device;
wherein the sensor device includes at least one detector element, and wherein the opening and the at least one detector element are disposed such that the x-ray beam. passing through the opening is allowed to strike only a portion of the at least one detector element capable of receiving the x-ray beam, the portion being less than 100% of a sensitive area of the at least one detector element;
wherein a change in output signal of the at least one detector element of the sensor device is responsive to a change in position and size of the area of x-ray allowed to fall on the at least one detector element of the sensor device in response to the movement of the focal spot;
wherein the change in output signal is a position indicator for the focal spot; and
wherein the opening is dimensioned to be approximately a pinhole.

4. The device of claim 3, wherein the sensor device includes a fluorescent screen, which faces the opening so that the x-ray beam strikes the fluorescent screen, and a position sensitive photodiode that is arranged between the fluorescent screen and a back wall of the housing.

5. The device of claim 4, wherein the fluorescent screen is optically coupled to the position sensitive photodiode.

6. The device of claim 5, wherein the fluorescent screen is optically coupled to the position sensitive photodiode by a transparent epoxy layer.

7. The device of claim 3, further comprising a control mechanism in electronic communication with the sensor device.

8. The device of claim 7, wherein the control mechanism calculates the focal spot movement and compensates for detector response error induced by focal spot movement.

9. A focal spot sensing device comprising:
a housing that resists x-ray beams;
an opening disposed in the housing that allows an x-ray beam to enter the housing;
a first means responsive to the x-ray beam allowed to enter the housing for calculating a position of a focal spot; and
a second means responsive to the x-ray beam allowed to enter the housing for further calculating the position of the focal spot;
wherein the opening is sized such that the x-ray beam at a surface of the first means for calculating and at a surface of the second means for calculating is less than a total sensitive area of the first means for calculating and the second means for calculating;
wherein an area of the x-ray is allowed to fall on the first means and the second means for calculating such that the area changes in both position and size at the first means and the second means for calculating in response to movement of the focal spot in a plane parallel to the plane of the first means and the second means for calculating;
wherein the first means for calculating is aligned with a first axis, the second means for calculating is aligned with a second axis, the first axis is perpendicular to the second axis, and the first and second axes define a plane parallel to the first means and the second means for calculating;
wherein the first means and the second means for calculating each include at least two detector elements arranged next to each other and the opening is sized so that the x-ray beam strikes more than one of the at least two detector elements of each means for calculating, but only a portion of each detector element, the portion being less than 100% of a sensitive area of an associated detector element;
wherein a change in output signal of each detector element of the first means and the second means for calculating is responsive to a change in position and size of the area of x-ray allowed to fall on each detector element of the first means and the second means for calculating in response to the movement of the focal spot; and
wherein the change in output signal is a position indicator for the focal spot in two dimensions.

10. The device of claim 9, wherein the means for calculating includes a fluorescent screens, which faces the opening so that the x-ray beam strikes the fluorescent screen, and a position sensitive photodiode that is arranged between the fluorescent screen and a basic wall of the housing; and the opening is dimensioned to be approximately a pinhole.

11. The device of claim 10, wherein the fluorescent screen is optically coupled to the position sensitive photodiode by a transparent epoxy layer.

12. The device of claim 9, further comprising a control mechanism in electronic communication with the means for calculating a position of a focal spot.

13. The device of claim 12, wherein the control mechanism calculates the focal spot movement and compensates for detector response error induced by focal spot movement.

14. An imaging system comprising:
an x-ray source that produces an x-ray beam and has a focal spot;
a detector array that receives the x-ray beam and includes a focal spot sensing device, the focal spot sensing device includes: a housing that resists x-ray beams; an opening disposed in a wall of the housing that allows the x-ray beam to enter the housing; and a sensor device disposed in the housing that interprets a position of the x-ray beam for calculating a position of the focal spot, the sensor device being disposed in the housing such that an area of the x-ray allowed to fall on the sensor device changes in both position and size at the sensor device in response to movement of the focal spot in a plane parallel to the plane of the sensor device;
wherein the opening is sized such that the x-ray beam at a surface of the sensor device is less than a total sensitive area of the sensor device;
wherein the sensor device includes at least one detector element and the opening is sized so that the x-ray beam strikes only a portion of the at least one detector element, the portion being less than 100% of a sensitive area of the at least one detector element;
wherein a change in output signal of the at least one detector element of the sensor device is responsive to a change in position and size of the area of x-ray allowed to fall on the at least one detector element of the sensor device in response to the movement of the focal spot;
wherein the change in output signal is a position indicator for the focal spot;
wherein the sensor device includes a fluorescent screen, which faces the opening so that the x-ray beam strikes the fluorescent screen, and a position sensitive photodiode that is arranged between the fluorescent screen and a back wall of the housing; and
wherein the opening is dimensioned to be approximately a pinhole.

15. The system of claim 14, wherein the fluorescent screen is optically coupled to the position sensitive photodiode by a transparent epoxy layer.

16. A method for sensing a focal spot, the method comprising:
receiving an x-ray beam into an opening of a focal spot sensing device, the focal spot sensing device having a sensor device;
receiving the x-ray beam at the sensor device disposed in the focal spot sensing device, wherein the sensor device includes at least three detector elements arranged on two orthogonal axes such that the x-ray beam passing through the opening is allowed to strike more than two of the at least three detector elements, but only a portion of each, the portion being less than 100% of a sensitive area of an associated detector element;
measuring a change in output signal of each detector element in response to a change in position and size of the area of x-ray allowed to fall on each detector element in response to the movement of the focal spot;
interpreting a position of the x-ray beam; and calculating a position in two dimensions of the focal spot in response to an area of the x-ray beam allowed to fall on the sensor device changing in both position and size at the sensor device in response to movement of the focal spot in a plane parallel to the plane of the sensor device;

wherein a change in output signal of the sensor device is responsive to a change in position and size of the area of x-ray allowed to fall on the sensor device in response to the movement of the focal spot; and wherein the change in output signal is a position indicator for the focal spot in two dimensions.

17. The method of claim 16, further comprising calibrating a CT system detector in response to the position of a focal spot.

18. The method of claim 16, further comprising receiving the x-ray beam at the sensor device disposed in the focal spot sensing device, the sensor device includes a fluorescent screen, which faces the opening so that the x-ray beam strikes the fluorescent screen, and a position sensitive photodiode that is arranged between the fluorescent screen and a back wall of the focal spot sensing device.

* * * * *